United States Patent [19]
Arrigo

[11] Patent Number: 6,057,095
[45] Date of Patent: May 2, 2000

[54] SCREENING PROCEDURE FOR INHIBITORS OF HIV REV FUNCTION

[75] Inventor: Salvatore J. Arrigo, Mt. Pleasant, S.C.

[73] Assignee: Medical University of South Carolina, Charleston, S.C.

[21] Appl. No.: 08/893,793

[22] Filed: Jul. 11, 1997

[51] Int. Cl.[7] .............................. C12Q 1/70; C12Q 1/68
[52] U.S. Cl. ................................ 435/5; 435/6; 436/501; 536/23.4; 536/23.72
[58] Field of Search .................................. 435/5, 6, 501; 536/23.4, 23.72

[56] References Cited

U.S. PATENT DOCUMENTS 5,534,408  7/1996  Green et al. ................................. 435/5

OTHER PUBLICATIONS

Ciccarelli etal., *Antiviral Chem. Chemother.* 5(3): 169–175, 1994.

Arrigo et al. "Analysis of rev gene function on human immunodeficiency virus type 1 replication in lymphoid cells by using a quantitative polymerase chain reaction method" *J. Virol.* 63:4875–4881, 1989.

Arrigo et al. "Rev is necessary for translation but not cytoplasmic accumulation of HIV–1 vif, vpr, and env/vpu 2 RNAs." *Genes Dev.* 5:808–819, 1991.

Raghavendar et al. "Identification and mapping of inhibitory sequences in the human immunodeficiency virus type 2 vif gene" *J. Virol.* 69:5167–5170, 1995.

Cochrane et al. "Identification and characterization of intragenic sequences which repress human immunodeficiency virus structural gene expression" *J. Virol.* 65:5305–5313, 1991.

Bürki, K. "Genetically engineered cells and animals: new tools in pharmacology" *Int. Pharm. J.* 9:Suppl.1,4.

Shukla et al. "Human chromosome 6– and 11–encoded factors support human immunodeficiency virus type 1 function in A9 cells" *J. Virol.* 70:9064–9068, 1996.

Schiller et al. "Rapid complementation assay for anti––HIV–1 drug screening and analysis of envelope protein function" *Aids Res. Hum. Retro.* 8:1723–1731, 1992.

Helseth et al. "Rapid complementation assays measuring replicative potential of human immunodeficiency virus type 1 envelope glycoprotein mutants" *J. Virol.* 64:2416–2420, 1990.

Bahner et al. "Comparison of trans–dominant inhibitory mutant human immunodeficiency virus type 1 genes expressed by retroviral vectors in human T lymphocytes" *J. Virol.* 67:3199–3207, 1993.

Xiaobin et al. "Assay systems for HIV Rev function using chimeric gene constructions" *V Int. Conf. on AIDS*, Jun. 4–9 (1262p) 1989.

*Primary Examiner*—Robert D. Budens
*Attorney, Agent, or Firm*—Needle & Rosenberg, P.C.

[57] ABSTRACT

This invention provides a method of screening for inhibitors of HIV Rev function, comprising introducing into a cell a nucleic acid construct comprising a reporter gene positioned in the construct such that expression of the reporter gene increases when Rev function decreases and wherein the cell contains Rev, administering to the cell a potential inhibitor of Rev function, monitoring the expression of the reporter gene, and correlating the expression of the reporter gene to an inhibition of Rev function. Also provided is a method of screening for inhibitors of HIV Rev function, further comprising introducing into a second cell a second nucleic acid construct comprising a reporter gene wherein Rev does not affect the expression of the reporter gene of the second nucleic acid construct, administering to the cells a potential inhibitor of Rev function, monitoring the expression of the reporter genes, correcting the expression of the reporter gene in the first nucleic acid construct by the expression of the reporter gene in the second nucleic acid construct, and correlating the corrected expression of the reporter gene in the first nucleic acid construct to an inhibition of Rev function. The invention also provides a method for monitoring expression of regulatory genes of HIV relative to structural genes, a method of screening for inhibition of the function of a Rev-responsive element (RRE), and isolated nucleic acid constructs comprising an HIV RRE and a reporter gene positioned such that expression of the reporter gene decreases when Rev protein interacts with the RRE.

4 Claims, 2 Drawing Sheets

SCREENING PROCEDURE FOR INHIBITORS OF HIV REV FUNCTION

BACKGROUND OF THE INVENTION

1. Field of the Invention

This invention generally relates to methods for screening for inhibitors of HIV Rev function. Specifically, this invention relates to a method of screening for inhibitors of HIV Rev function using a nucleic acid construct comprising a reporter gene positioned in the construct such that expression of the reporter gene increases when Rev function is decreased.

2. Background Art

Acquired Immune Deficiency Syndrome (AIDS), a fatal human disease, is generally considered to be one of the more significant diseases to affect humankind, and has affected numerous individuals worldwide. Because this disease is so widespread and so destructive, there is a vast amount of research currently being undertaken to find new therapies and new drugs which may provide some assistance in combating this virus. One approach for drug therapy is to target viral proteins in an attempt to inhibit or halt viral replication.

One of the viral proteins that is required for viral replication is Rev. This protein is necessary for high-level production of the gag and env structural proteins. One hypothesis concerning regulation of HIV gene expression is that Rev facilitates transport and stability of unspliced or singly spliced RNAs from the nucleus to the cytoplasm where these RNAs are subsequently translated. (Knight et al. "Expression of the art/trs protein of HIV and study of its role in viral envelope synthesis" Science 236:837–840 (1987) and Malim et al. "The HIV-1 rev trans-activator acts through a structural target sequence to activate nuclear export of unspliced viral mRNA" Nature 338:254–257 (1989)). These observations, however, may be a result of the specific model systems utilized in those studies since Arrigo et al. found that Rev did not appear to affect the cytoplasmic level of singly spliced vif, vpr, or env/vpu 2 RNAs in lymphoid cells, but appeared to regulate the assembly of these transcripts into polysomes for translation. (Arrigo et al. "Rev is necessary for translation but not cytoplasmic accumulation of HIV-1 vif, vpr, and env/vpu 2 RNAs" Genes and Develop. 5:808–819 (1991)). Therefore Rev may have more than one mode for regulating HIV gene expression. Whatever specific mechanism or mechanisms by which Rev acts, it is clear that Rev has a major role in HIV gene expression since Rev-deficient mutants of HIV are unable to produce infectious virions and trans-dominant Rev mutants are able to down-regulate the activity of wild-type Rev. ("Textbook of AIDS Medicine" Ed. Broder et al. Pub. by Williams and Wilkins, Baltimore, Md. (1994) and Malim et al. "Functional dissection of the HIV-1 Rev trans-activator—derivation of a trans-dominant repressor of Rev function" Cell 58:205–214 (1989)). Inhibition of Rev function is therefore a clear candidate for drug or inhibitor targeting for therapeutic and prophylactic purposes, but screening compounds or compositions for inhibition of Rev function requires an effective and practical assay.

Previously utilized assays for Rev function include filter binding assays, gel mobility (gel shift) assays, spectroscopic assays, and capture assays. (See, e.g., WO 92/05195). These assays are relatively tedious and expensive, generally insensitive, and labor intensive. These assays are also relatively unsuitable for large scale, high volume assays involving multiple tests.

Similarly, assays for evaluating Rev function comprising nucleic acid amplification techniques are also labor intensive, relatively expensive, and generally unsuitable for large scale, high volume assays. (See, e.g., Arrigo et al. "Analysis of rev gene function on human immunodeficiency virus type 1 replication in lymphoid cells by using a quantitative polymerase chain reaction method" J. Virol. 63:4875–4881 (1989)). These assays have the additional drawback of being limited to monitoring nucleic acid levels which are not necessarily related to the activity of a gene product.

Assays utilizing reporter genes have also been used in Rev-related studies. For example, see Raghavendar et al. "Identification and mapping of inhibitory sequences in the human immunodeficiency virus type 2 vif gene" J. Virol. 69:5167–5170 (1995), Cochrane et al. "Identification and characterization of intragenic sequences which repress human immunodeficiency virus structural gene expression" J. Virol. 65:5305–5313 (1991), Shukia et al. "Human chromosome 6- and 11-encoded factors support human immunodeficiency virus type 1 function in A9 cells" J. Virol. 70:9064–9068 (1996), Schiller et al "Rapid complementation assay for anti-HIV-1 drug screening and analysis of envelope protein function" Aids Res. Hum. Retro. 8:1723–1731 (1992), and U.S. Pat. No. 5,534,408 "2-Deoxystreptamine aminoglycoside inhibition of HIV/Rev binding," all of which utilize a chloramphenicol aminotransferase (CAT) assay where the activity of the chloramphenicol aminotransferase is positively correlated to Rev function. Additionally, see Bahner et al. "Comparison of trans-dominant inhibitory mutant human immunodeficiency virus type 1 genes expressed by retroviral vectors in human T lymphocytes" J. Virol. 67:3199–3207 (1993) and Xiaobin et al. "Assay systems for HIV Rev function using chimeric gene constructions" V Int. Conf. on AIDS, Jun. 4–9, 1989, p. 1262, which utilize the *Escherichia coli* lacZ gene operatively linked to an HIV gene wherein the expression of the lacZ reporter gene is positively correlated to Rev function.

The present invention provides a novel method in which the expression of the reporter gene increases with an increasing inhibition of Rev function, thereby providing a method with significantly more sensitivity than previously available techniques. Additionally, the methods provided by the present invention have the capacity to discriminate between an effect which is not Rev-specific which might indirectly affect the level of the reporter activity and a Rev-specific effect. Therefore the methods provided herein represent an important improvement over the art by providing a much needed means to evaluate potential anti-Rev drugs as well as providing a method by which one can screen for the inhibition of a Rev responsive element and a method by which one can monitor the expression of HIV structural genes relative to HIV regulatory genes.

SUMMARY OF THE INVENTION

In accordance with the purpose(s) of this invention, as embodied and broadly described herein, the invention, in one aspect, provides a method of screening for inhibitors of HIV Rev function, comprising introducing into a cell a nucleic acid construct comprising a reporter gene wherein the reporter gene is positioned in the construct such that expression of the reporter gene is increased when Rev function is decreased and wherein the cell contains Rev, administering to the cell a potential inhibitor of Rev function, monitoring the expression of the reporter gene, and correlating the expression of the reporter gene to an inhibition of Rev function.

The invention further provides a method of screening for inhibitors of HIV Rev function, comprising introducing into a cell a nucleic acid construct comprising a reporter gene wherein the reporter gene is positioned in the construct such that expression of the reporter gene is increased when Rev function is decreased and wherein the cell contains Rev, administering to the cell a potential inhibitor of Rev function, monitoring the expression of the reporter gene, and correlating the expression of the reporter gene to an inhibition of Rev function, further comprising introducing into a second cell a nucleic acid construct comprising a reporter gene wherein Rev does not affect the expression of the reporter gene, administering to the second cell a potential inhibitor of Rev function, monitoring the expression of the reporter gene, and correlating a change in the expression of the reporter gene to an effect of the potential inhibitor not associated with an inhibition of Rev function.

The invention also provides a method of screening for inhibitors of HIV Rev function, comprising introducing into a first cell a first nucleic acid construct comprising a reporter gene and introducing into a second cell a second nucleic acid construct comprising a reporter gene, wherein the reporter gene of the first nucleic acid is positioned in the construct such that expression of the reporter gene is increased when Rev function is decreased and wherein Rev does not affect the expression of the reporter gene of the second nucleic acid construct, administering to the cells a potential inhibitor of Rev function, monitoring the expression of the reporter genes, correcting the expression of the reporter gene in the first nucleic acid construct by the expression of the reporter gene in the second nucleic acid construct, and correlating the corrected expression of the reporter gene in the first nucleic acid construct to an inhibition of Rev function, thereby screening for inhibitors of HIV Rev function.

The invention also provides a method for monitoring expression of regulatory genes of HIV relative to the expression of structural genes of HIV, comprising introducing into a cell a nucleic acid construct comprising a reporter gene positioned in the construct whereby expression of the reporter gene is increased when Rev function is decreased, monitoring the expression of the reporter gene, and correlating the expression of the reporter gene to expression of regulatory genes of HIV relative to expression of structural genes of HIV.

The invention also provides a method of screening for inhibition of the function of a Rev-responsive element, comprising introducing into a cell a nucleic acid construct comprising a Rev-responsive element and a reporter gene which are positioned in the construct whereby expression of the reporter gene is increased when the Rev-responsive element is functional and interacts with Rev, administering to the cell a potential inhibitor of Rev-responsive element, monitoring the expression of the reporter gene, and correlating the expression of the reporter gene to an inhibition of the Rev-responsive element, thereby screening for inhibition of the function of a Rev-responsive element, thereby screening for inhibition of the function of a Rev-responsive element.

Also provided by the present invention is an isolated nucleic acid construct comprising an HIV Rev-responsive element and a reporter gene, wherein the Rev-responsive element and the reporter gene are positioned in the construct such that expression of the reporter gene is decreased when Rev protein interacts with the Rev-responsive element.

DETAILED DESCRIPTION OF THE INVENTION

Figure 1:
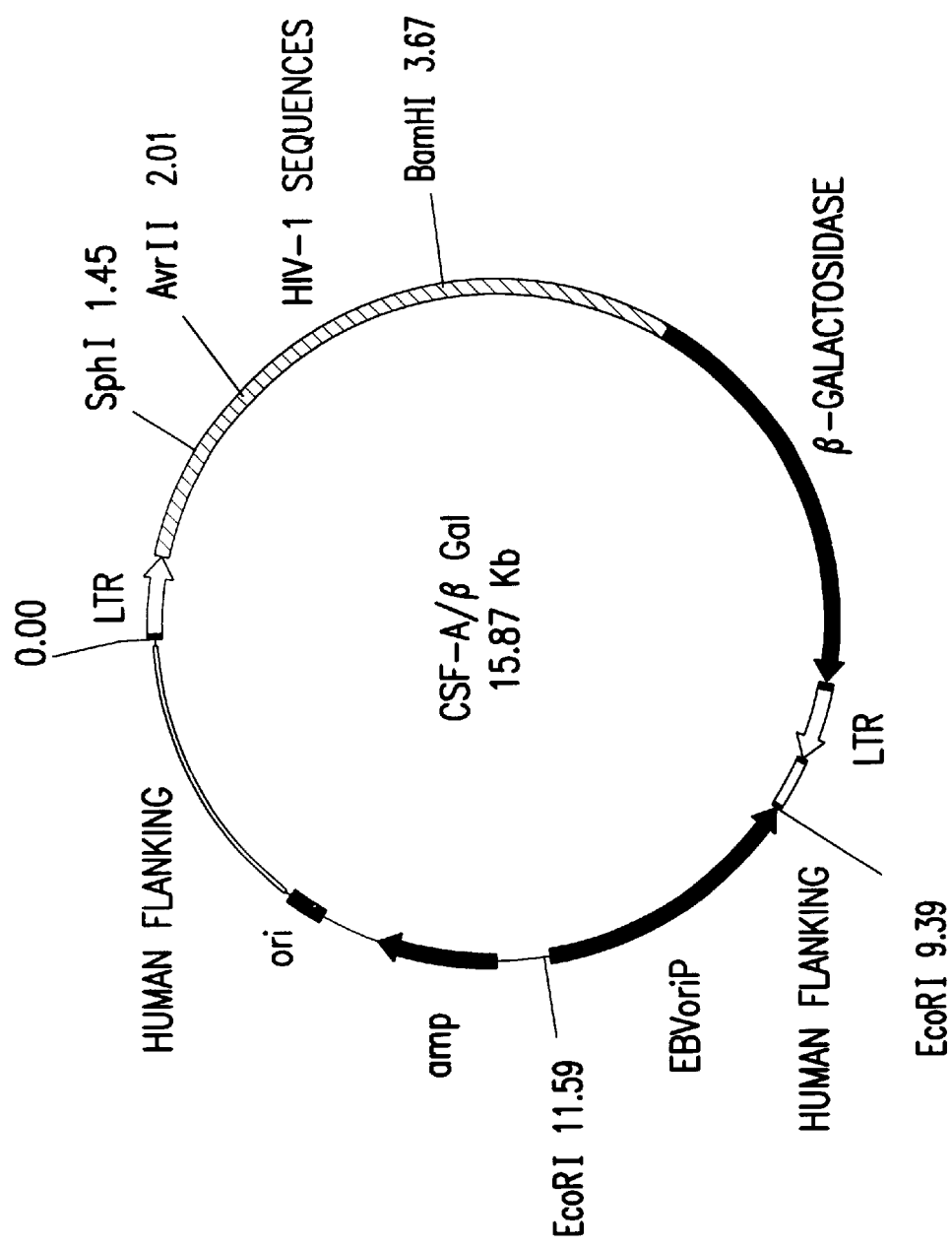
FIG. 1 shows the map of plasmid CSF-A/βGal. The amp region represents the ampicillin resistance gene; ori represents an *Escherichia coli* origin of replication; the two LTRs represent HIV long terminal repeats; the region between the two LTRs designated HIV-1 sequences represents sequences derived from pYKJRCSF, an infectious molecular clone of HIV from which the polymerase gene has been deleted and sequences encoding β-galactosidase inserted into the nef gene; the two human flanking regions represent human sequences flanking HIV integration sites derived from the original HIV clone; and the EBVoriP region represents the episomal origin of replication of Epstein-Barr virus.

The present invention may be understood more readily by reference to the following detailed description of the preferred embodiments of the invention and the Examples included therein and to the Figures and their previous and following description.

Before the present methods are disclosed and described, it is to be understood that this invention is not limited to specific cells, specific detection methods, or specific nucleic acid constructs, as such may, of course, vary, and the numerous modifications and variations therein will be apparent to those skilled in the art. It is also to be understood that the terminology used herein is for the purpose of describing particular embodiments only and is not intended to be limiting.

As used in the specification and in the claims, "a" can mean one or more, depending upon the context in which it is used. Thus, for example, reference to "a cell" means that at least one cell is utilized.

In one aspect, the invention provides a method of screening for inhibitors of HIV Rev function, comprising introducing into a cell a nucleic acid construct comprising a reporter gene wherein the reporter gene is positioned in the construct such that expression of the reporter gene is increased when Rev function is decreased and wherein the cell contains Rev, administering to the cell a potential inhibitor of Rev function, monitoring the expression of the reporter gene, and correlating the expression of the reporter gene to an inhibition of Rev function.

The terms "expression" or "gene expression" are used herein to describe both transcription and translation, as well as an activity of a protein or enzyme. For example, where a gene is expressed, that expression can be monitored by monitoring the presence of or the level of transcription. For example, the production of RNA can be monitored, even quantitatively, through techniques such as RNA hybridization or amplification. Gene expression also describes the translation of an RNA with concurrent production of a polypeptide, which is typically a protein or an enzyme. These proteins or enzymes can be monitored using such techniques as assaying for a particular enzyme activity, or by the presence of a protein or polypeptide through assays such as immmunodetection or fluorescence detection. Alternatively, the presence of a protein or enzyme can be detected through an indirect or at least a secondary interaction or effect which can be correlated to the presence of the protein or enzyme. Therefore monitoring gene expression encompasses both qualitative accessing gene expression as well as quantitative measurement of gene expression. Using the methods described herein, one skilled in the art can administer differing dosages of an inhibitor of Rev-function or an inhibitor of a Rev-responsive element to obtain quantitative data which can be used to generate a dose-response curve. These methods can therefore be standardized and a potential inhibitor of Rev-function or of the Rev-responsive element can be evaluated in relation to a standard.

The term "Rev function" encompasses anything in the pathway from the expression of Rev itself to a Rev effect on the ultimate expression from RNA transcripts. While not intending to be bound by theory, the mechanism of Rev appears to be multifaceted including affecting splicing in some experimental systems, facilitating the cytoplasmic accumulation of RNAs containing an RRE in a variety of model systems, affecting the cytoplasmic stability of RNAs, and affecting the assembly of RNA transcripts into polysomes for subsequent translation. Therefore an inhibitor of Rev function may, for example, act at the binding step with the result being a decrease in expression of unspliced or singly spliced HIV transcripts. Alternatively, an inhibitor of Rev function may act by inhibiting the transport of unspliced or singly spliced HIV transcripts from the nucleus to the cytoplasm through a different mechanism. Each of these exemplary control points comprise a Rev function which can be a target for an inhibitor of Rev function. One skilled in the art will, however, recognize that alternative Rev effects are possible and "Rev function" as used herein will include those effects as well. The present invention provides methods by which one can screen for inhibitors of Rev function and the precise mechanism of action of any such inhibitor is not necessarily relevant to the method itself The methods provided herein, therefore, may be used to screen for an inhibitor of Rev function regardless of the mode of action of the inhibitor.

Similarly, the function of the Rev-responsive element (RRE) encompasses anything which is associated with the Rev-responsive element which affects its ability to interact with Rev and result in the expression of unspliced or singly spliced HIV transcripts. For example, an antisense nucleic acid targeted to the Rev-responsive element may affect the function of the Rev-responsive element since it is believed that the Rev-responsive element forms a stem-loop secondary structure with which Rev interacts. This antisense may bind to the Rev-responsive element, or a portion thereof, and disrupt the native secondary structure such that Rev cannot effectively bind to the Rev-responsive element.

The term "inhibitors" is familiar to one skilled in the art and is used herein to describe any compound or composition which inhibits or decreases Rev function or inhibits or decreases the function of the Rev-responsive element. Rev is known in the art to bind to the Rev-responsive element with the result being the expression from unspliced or singly spliced HIV transcripts and an inhibitor of Rev function comprises anything which can either directly or indirectly interfere with that process. The methods described herein, however, are not limited to an HIV context regarding the nucleic acids since Rev function can occur in any nucleic acid context as long as the necessary elements are present; the Rev-responsive element for example.

The methods described herein comprise introducing into a cell a nucleic acid construct. One skilled in the art will recognize that this aspect of the methods can comprise either a stable or a transient introduction of the nucleic acid construct into the cell. Additionally, the stably or the transiently introduced nucleic acid may or may not become integrated into the genome of the host. One skilled in the art will also recognize that the precise procedure for introducing the nucleic acid into the cell may, of course, vary and may depend on the specific type or identity of the cell. Examples of methods for introducing a nucleic acid into a cell include, but are not limited to electroporation, cell fusion, DEAE-dextran mediated transfection, calcium phosphate-mediated transfection, infection with a viral vector, microinjection, lipofectin-mediated transfection, liposome delivery, and particle bombardment. An example of introducing a nucleic acid into a cell by electroporation is described in the Example contained herein.

The nucleic acid construct can comprise a linear molecule, or the nucleic acid can be circular, such as a nucleic acid encoding a reporter gene within a nucleic acid vector. The nucleic acid construct should contain components necessary for expression of the nucleic acid such an appropriate promoter, but the nucleic acid construct may also contain other functional regions such as an origin of replication and/or an antibiotic resistance gene. One skilled in the art will recognize that certain cell types may express a certain nucleic acid more efficiently when the nucleic acid contains certain sequences which may be more efficiently expressed in that cell type.

Similarly, the nucleic acid construct may contain a sequence which encodes Rev. Therefore the cell into which the nucleic acid construct is introduced does not necessarily have to encode or otherwise produce Rev, such as a cell which is infected with HIV, in order to practice the invention. For example, one can introduce into a cell a nucleic acid construct which has a Rev-responsive element positioned within the nucleic acid construct such that the expression of a reporter gene on that same construct increases with increasing inhibition of Rev or the Rev-responsive element and wherein Rev is encoded by the same nucleic acid construct, another nucleic acid construct such as a second nucleic acid which is also introduced into the cell, the genome of a virus which is present in the cell, or even a protein which itself is administered to the cell.

The nucleic acid construct comprising a reporter gene wherein the reporter gene is positioned in the construct such that the expression of the reporter gene is increased when Rev function is decreased may be obtained in any number of techniques known to one skilled in the art. One method of constructing the nucleic acid construct is to synthesize a recombinant DNA molecule. For example, oligonucleotide synthesis procedures are routine in the art and oligonucleotides coding for a particular protein or regulatory region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins or regulatory regions can be synthesized by first constructing several different double-stranded molecules that code for particular regions of the protein or regulatory region, followed by ligating these DNA molecules together. For example, Cunningham et al., "Receptor and Antibody Epitopes in Human Growth Hormone Identified by Homolog-Scanning Mutagenesis," *Science*, Vol. 243, pp. 1330–1336 (1989), have constructed a synthetic gene encoding the human growth hormone gene by first constructing overlapping and complementary synthetic oligonucleotides and ligating these fragments together. See also, Ferretti et al., Proc. Nat. Acad. Sci. 82:599–603 (1986), wherein synthesis of a 1057 base pair synthetic bovine rhodopsin gene from synthetic oligonucleotides is disclosed. Once the appropriate DNA molecule is synthesized, this DNA can be cloned downstream of a promoter in an appropriate orientation. Techniques such as this are routine in the art and are well documented.

An example of another method of obtaining the nucleic acid construct is to isolate that nucleic acid from the organism in which it is found and clone it in an appropriate vector. For example, a DNA or CDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Yet another example of a method of obtaining the nucleic acid construct is to amplify a nucleic acid from the nucleic acids found within a host organism, such as the specific reporter and/or a specific provirus nucleic acid, and clone the amplified nucleic acid in an appropriate vector. One can the modify the cloned nucleic acid, if necessary, such as adding a host-specific promoter or repositioning the cloned nucleic acid such that the interaction of Rev with the Rev- responsive element results in a decrease in the expression of the particular reporter gene. Given the teachings of the present disclosure and the present constructs, one skilled in the art can obtain a nucleic acid construct utilizing commercially available nucleic acids such as plasmids and copies of proviral nucleic acids, as well as commercially available reporter genes. One skilled in the art can then combine these components using routine molecular protocols and modify the nucleic acids such as by the addition of linkers, as necessary or desirable. These techniques are well known in the art and exemplified in the Example section contained herein where the construction of a particular nucleic acid construct wherein a reporter gene is positioned in the construct such that the expression of the reporter gene is increased when Rev function is decreased is disclosed.

One skilled in the art will also recognize that the identity of the specific reporter gene can, of course, vary. Examples of various reporter genes that have been used to monitor gene expression include, but are not limited to genes encoding an enzymatic activity such as the chloramphenicol acetyltransferase (CAT) gene, luciferase (luc), β-galactosidase, horseradish peroxidase, or alkaline phosphatase. Alternatively, the reporter gene may comprise a fluorescent label such as FITC, rhodamine, lanthanide phosphors, or a green fluorescent fusion protein (See, e.g., Stauber et al. "Analysis of trafficking of Rev and transdominant Rev proteins in living cells using green fluorescent protein fusions: transdominant Rev blocks the export of Rev from nucleus to cytoplasm" Virol. 213:439–449 (1995)). Alternatively, the reporter may comprise a predetermined polypeptide epitope which can be recognized by a secondary reporter such as leucine zipper pair sequences, binding sites for secondary antibodies, metal binding domains, or epitope tags. One skilled in the art will appreciate that the specific reporter gene or genes utilized in the methods disclosed herein may vary and may also depend on the specific model system utilized, and the methods disclosed herein are not limited to any specific reporter gene or genes.

One skilled in the art will recognize that compounds comprising nucleic acid constructs comprising a reporter gene wherein the reporter gene is positioned in the construct such that the expression of the reporter gene is increased when Rev function is decreased are also provided by the present invention. A compound comprising a nucleic acid can be a derivative of a typical nucleic acid such as nucleic acids which are modified to contain a terminal or an internal reporter molecule or those nucleic acids containing nontypical bases or sugars. These reporter molecules include, but are not limited to isotopic and non-isotopic reporter molecules. Any molecule which may aid in detection, amplification, replication, expression, purification, uptake, etc. may be added to the nucleic acid construct.

One skilled in the art will also appreciate that the nucleic acid constructs of the methods disclosed herein and in the compounds comprising the nucleic acid constructs contain a Rev-responsive element positioned in the nucleic acid constructs such that when Rev interacts with or binds to the Rev-responsive element, that interaction or binding results in a decrease in the expression of the reporter gene. For example, and as described in the Example contained herein, the reporter gene can be placed downstream from the Rev-responsive element such that where Rev function is not inhibited, translation of the nucleic acid transcript encoding the reporter gene is initiated at the upstream initiation codon, and where Rev function is inhibited, translation of the gene transcript is initiated at the reporter gene initiation codon and therefore an active reporter protein is produced. In this specific example, the downstream reporter gene initiation codon can be spaced at a distance from the upstream initiation codon such that translation initiation at reporter gene initiation codon in unspliced or singly spliced transcripts is a rare or nonexistent occurrence, and/or the downstream reporter gene initiation codon can be in a different reading frame than the upstream initiation codon such that translation initiated at the upstream initiation codon does not produce an active reporter protein. Alternatively, the reporter gene can be interrupted by an intron such that when the intron is spliced out of the transcript as a result of an inhibition of Rev function, the reporter gene coding sequence is restored and in frame and translation of this spliced message results in production of the protein encoded by the reporter gene. Alternatively, the reporter gene can be placed within, or partially within, an intron that is removed by RNA splicing where unspliced or singly spliced messages are expressed. An additional possibility is that a sequence in the nucleic acid construct promotes the expression of the reporter gene and that Rev function removes or inhibits this promotion of expression of the reporter gene, therefore when Rev function is inhibited, expression of the reporter gene is increased relative to where Rev function is present. One skilled in the art will appreciate that given the present disclosure there are numerous possibilities where an inhibition of Rev function results in the increased expression of a reporter gene relative to where Rev function is present and the compounds comprising nucleic acid constructs and the nucleic acid constructs utilized in the methods described herein are not limited to the specific examples described herein.

The cell to which the nucleic acid is introduced and to which a potential inhibitor is administered may comprise a cell ex vivo, such as a cell removed from a subject which is administered the potential inhibitor and subsequently replaced back in the subject. Alternatively, the cell may comprise a cell in vivo, such as delivering the potential inhibitor to a cell within a subject. Alternatively, the cell may comprise a cell in culture, such as an established tissue culture cell line or even a cell removed from a subject which has not been adapted to tissue culture. The precise conditions or environment in which the cell is maintained is not limiting to the methods of the present invention.

The compounds or compositions that represent potential inhibitors of Rev function can be administered to a cell in any number of ways. For example, the compound or composition can be added to the medium in which the cell is growing, such as tissue culture medium for cells grown in culture. Alternatively, the potential inhibitor may be encoded by a nucleic acid that is introduced into the cell wherein the cell essentially produces the potential inhibitor itself.

Where the potential Rev function inhibitor is administered to a cell in vivo, the method of introducing that potential inhibitor can also vary. For example, a Rev function inhibitor, or a pharmaceutical composition comprising a Rev function inhibitor can be administered by topical intranasal administration. The Rev function inhibitor may also be administered orally, parenterally (e.g., intravenously), by intramuscular injection, by intraperitoneal injection, topically, transdermally, or the like. The exact amount of a Rev function inhibitor required may vary from subject to subject, depending on the age, weight and general condition of the subject, the severity of the infection that is being treated, the particular compound used, its mode of administration and the like. Thus, it is not possible to specify an exact amount. However, an appropriate amount may be determined by one of ordinary skill in the art using only routine experimentation given the teachings herein.

In another aspect, the invention provides a method of screening for inhibitors of HIV Rev function, comprising introducing into a cell a nucleic acid construct comprising a reporter gene wherein the reporter gene is positioned in the construct such that expression of the reporter gene is increased when Rev unction is decreased and wherein the cell contains Rev, administering to the cell a potential inhibitor of Rev function, monitoring the expression of the reporter gene, correlating the expression of the reporter gene to an inhibition of Rev function, introducing into a second cell a nucleic acid construct comprising a reporter gene wherein Rev does not affect the expression of the reporter gene, administering to the second cell a potential inhibitor of Rev function, monitoring the expression of the reporter gene, and correlating a change in the expression of the reporter gene to an effect of the potential inhibitor not associated with an inhibition of Rev function.

This method correlates the expression of the reporter gene in the cell which contains Rev to an inhibition of Rev function, and correlates the expression of the reporter gene which is not affected by Rev function to an effect of the potential inhibitor not associated with an inhibition of Rev function, and therefore can be used to correct or adjust the correlation of the expression of the reporter gene in the cell which contains Rev to a specific inhibition of Rev function. By "specific" inhibition of Rev function is meant that an inhibition of the expression of the reporter gene reflects an inhibition of Rev function versus some indirect or secondary effect such as a general inhibition of gene expression or a general cellular toxicity.

One skilled in the art will appreciate that where two reporter genes are introduced into cells, the reporter genes may be the same or encode the same polypeptide, or these reporter genes may be different or encode different polypeptides. The exact identity of the reporter gene may vary depending on the identity of the cell into which the reporter gene is being introduced which will be apparent to one skilled in the art. For example, where more than one nucleic acid construct is introduced into a cell, the reporter genes may be different in order to distinguish the expression of one reporter gene from another reporter gene.

In another aspect, the present invention therefore provides a method of screening for inhibitors of HIV Rev function, comprising introducing into a first cell a first nucleic acid construct comprising a reporter gene and introducing into a second cell a second nucleic acid construct comprising a reporter gene, wherein the reporter gene of the first nucleic acid is positioned in the construct such that expression of the reporter gene is increased when Rev function is decreased and wherein Rev does not affect the expression of the reporter gene of the second nucleic acid construct, administering to the cells a potential inhibitor of Rev function, monitoring the expression of the reporter genes, correcting the expression of the reporter gene in the first nucleic acid construct by the expression of the reporter gene in the second nucleic acid construct, and correlating the corrected expression of the reporter gene in the first nucleic acid construct to an inhibition of Rev function, thereby screening for inhibitors of HIV Rev function.

One skilled in the art will appreciate that the second nucleic acid construct can serve as a control for an effect by a potential inhibitor of Rev-function or a potential inhibitor of a Rev-responsive element that is an indirect effect, such as an overall effect on RNA splicing within the cell. For example, where expression of the reporter gene of the second nucleic acid construct increases after administering a potential inhibitor to a cell containing that nucleic acid construct, this increased gene expression can be attributed to an effect not associated with an inhibition of Rev-function or an inhibition of the function of the Rev-responsive element. Therefore the expression of the reporter gene of the first nucleic acid construct can be corrected, lowered in this example, by the level of expression of the reporter gene in the second nucleic acid construct.

Given the present disclosure, one skilled in the art will appreciate that one can introduce into a cell a nucleic acid construct comprising a reporter gene positioned in the construct whereby expression of the reporter gene is increased when Rev function is decreased in order to monitor the expression of HIV regulatory genes relative to HIV structural genes. It is known in the art that HIV expresses regulatory genes early in a cell infection and only after REV has been expressed to a sufficient level does gene expression of the HIV structural genes become predominant. The nucleic acid constructs of the present invention can, therefore, be used to monitor this shift in gene expression in a cell infected with HIV or a cell into which a noninfectious copy of an HIV has been introduced.

Therefore, in yet another aspect, the present invention provides a method for monitoring expression of regulatory genes of HIV relative to the expression of structural genes of HIV, comprising introducing into a cell a nucleic acid construct comprising a reporter gene positioned in the construct whereby expression of the reporter gene is increased when Rev function is decreased, monitoring the expression of the reporter gene, and correlating the expression of the reporter gene to expression of regulatory genes of HIV relative to expression of structural genes of HIV.

Since the expression of the reporter gene in the methods and constructs provided herein requires an interaction between Rev and the Rev-responsive element, the present invention therefore also provides a method of screening for inhibition of the function of a Rev-responsive element, comprising introducing into a cell a nucleic acid construct comprising a Rev-responsive element and a reporter gene which are positioned in the construct whereby expression of the reporter gene is increased when the Rev-responsive element is functional and interacts with Rev, administering to the cell a potential inhibitor of Rev-responsive element, monitoring the expression of the reporter gene, and correlating the expression of the reporter gene to an inhibition of the Rev-responsive element, thereby screening for inhibition of the function of a Rev-responsive element.

The nature of the inhibitor of the Rev-responsive element is not limited to any type of compound, but an antisense nucleic acid is specifically contemplated since it is believed that the Rev-responsive element forms a stem-loop secondary structure with which Rev interacts. The antisense nucleic acid can comprise a typical nucleic acid, but the antisense nucleic acid can also be a modified nucleic acid or a derivative of a nucleic acid such as a phosphorothioate analogue of a nucleic acid.

The methods of the present invention may also be used to screen mutants of Rev or mutants of the Rev-responsive element. For example, one can introduce mutations into the Rev-responsive element and assay these mutants for function by positioning the mutant Rev-responsive element in a nucleic acid construct such that expression of a reporter gene is increased with decreasing ability of the Rev-responsive element to interact with Rev. Therefore the methods of the present invention can be used to screen not only potential inhibitors of Rev function or the Rev-responsive element, but these methods can be used to screen for mutant Rev protein or nucleic acids or mutant nucleic acids of the Rev-responsive element for their ability to function.

The present invention also provides an isolated nucleic acid construct comprising an HIV Rev responsive element and a reporter gene, wherein the Rev-responsive element and the reporter gene are positioned in the construct such that expression of the reporter gene is decreased when Rev protein interacts with the Rev-responsive element. The nucleic acid construct can also comprise a gene encoding a functional Rev protein. Additionally, the Rev protein encoded by a particular nucleic acid construct can be a trans-dominant Rev mutant. As used herein, "transdominant" means that the mutant can inhibit the function of a wild type Rev. For example, where a cell contains both a wild type Rev and a trans-dominant mutant of Rev, the function of the wild type Rev is inhibited whether the mutant Rev is provided either in cis or in trans.

Figure 2:
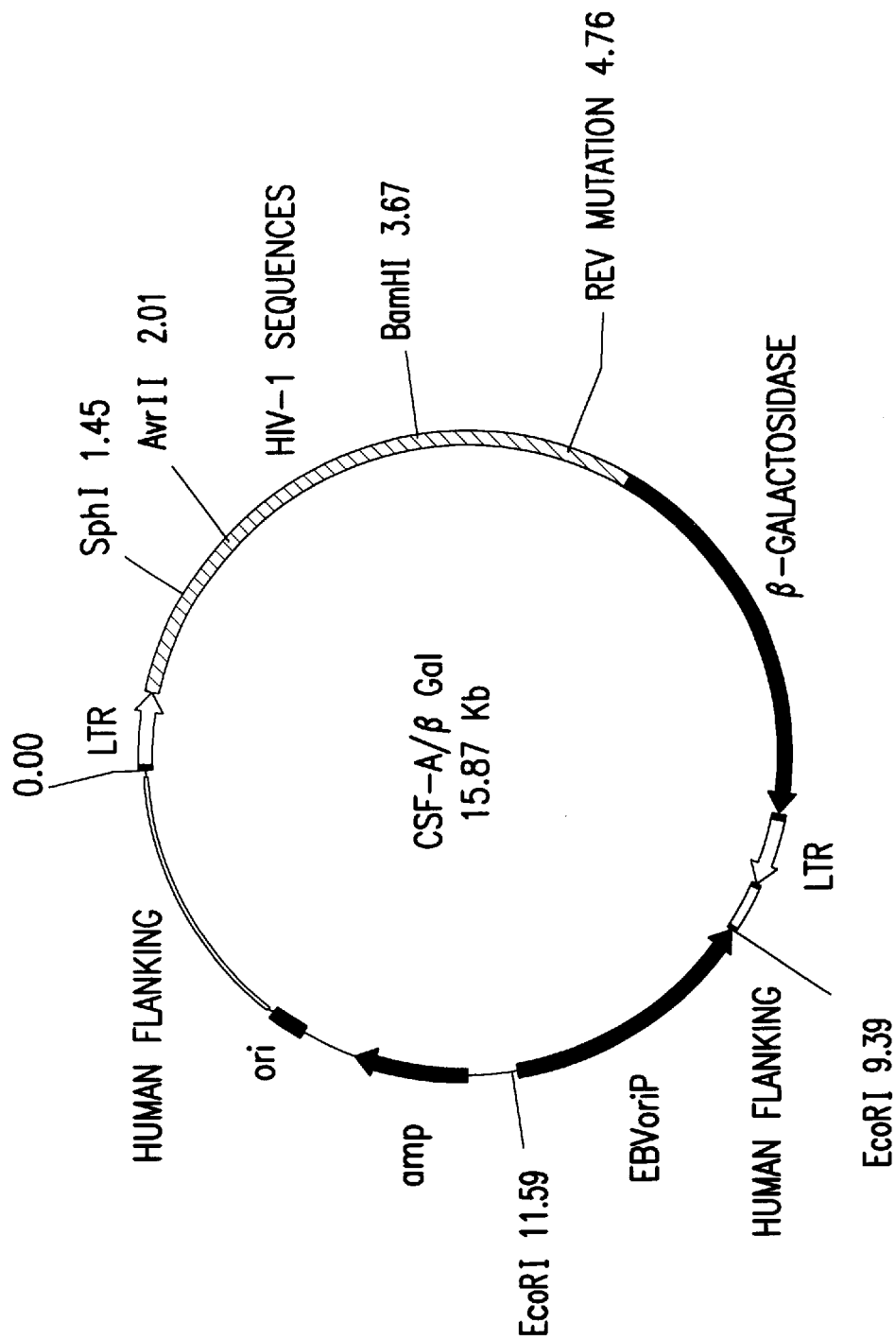
FIG. 2 shows the map of plasmid FS-A/βGal. The amp region represents the ampicillin resistance gene; ori represents an *Escherichia coil* origin of replication; the two LTRs represent HIV long terminal repeats; the region between the two LTRs designated HIV-1 sequences represents sequences derived from pYKJRCSF, an infectious molecular clone of HIV from which the polymerase gene has been deleted and sequences encoding β-galactosidase inserted into the nef gene; the two human flanking regions represent human sequences flanking HIV integration sites derived from the original HIV clone; and the EBVoriP region represents the episomal origin of replication of Epstein-Barr virus. This plasmid is essentially the same as plasmid CSF-A/βGal except plasmid FS-A/βGal contains a 4 base insertion at map unit 4.76 which inactivates Rev as the result of a frame shift mutation.

The nucleic acid constructs of the present invention can be obtained by any number of methods or procedures as discussed above and as exemplified by the construction of CSF-A/βGal and FS-A/βGal which are depicted in FIGS. 1 and 2, and as described in the Example contained herein.

Throughout this application, various publications are referenced. The disclosures of these publications in their entireties are hereby incorporated by reference into this application in order to more fully describe the state of the art to which this invention pertains.

The following example is put forth so as to provide those of ordinary skill in the art with a complete disclosure and description of how the nucleic acid constructs claimed herein are made and evaluated, and demonstrates the methods of the present invention, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE

To demonstrate an assay system suitable for the screening of compounds that are inhibitory to the Rev protein, we have utilized transient transfection with proviral constructs. All constructs were derived from an infectious molecular clone of HIV-1, pYKJRCSF (Koyanagi et al., 1987). The proviral construct was first mutated to eliminate over ⅓ of the viral sequences. (Arrigo and Huffinan 1995). The deletion encompasses the entire HIV-1 pol gene which results in a non-infectious construct that can be used under a reduced level of Biosafety containment (BL1-see NIH guidelines for Research Involving Recombinant DNA Molecules, April 1995) as compared to an infectious clone of HIV-1 (BL2-see NIH guidelines for Research Involving Recombinant DNA Molecules, April 1995). An easily assayable marker (β-galactosidase) was been inserted into the nef gene by inserting a SalI—SalI restriction enzyme-generated fragment from pMC1871 (Pharmacia) into the XhoI site of CSF-A by standard molecular cloning techniques. β-galactosidase is produced from the nef RNA as a fusion protein with the Nef protein in this construct. The construct was produced in both Rev-producing (CSF-A/β-gal) and Rev-deleted forms (FS-A/β-gal). The Rev-deleted form introduces a mutation into Rev that truncates the protein which results in a non-functional Rev protein. This construct was derived from CSF-A/β-gal by DR mutagenesis (Gatlin et al., 1995) using the following oligonucleotides:
5'-ACCACCGCGGGTTCACTAATTGTCCGGATC TGTCTC-3' (SEQ ID NO.1) and 5'-ACCACCGCGGATTCTTAGCACTTATCTGGGTCG-3' (SEQ ID NO.2).

Subsequent to PCR amplification with these oligonucleotide primers, the reaction was treated with SacII restriction endonuclease. The enzyme was inactivated by heat treatment and the reaction was treated with T4 DNA Ligase to circularize the PCR product. The reaction was then treated with DpnI restriction endonuclease to digest the template plasmid DNA. The reaction was then transformed into the HB 101 strain of *Escherichia coli* by electroporation. Ampicillin resistant colonies were propagated and screened by treatment with SacII restriction endonuclease to verify the insertion of the appropriate nucleotide sequence. The constructs contain an origin of replication from Epstein Barr Virus (EBV) that allows increased expression in the 729 B cell line (Arrigo et al., 1991). The mutation results in the insertion of 4 nucleotides (resulting in the creation of a SacII restriction enzyme site) into the Rev coding sequences which results in a frame-shift mutation and a premature termination of Rev. This frame shift mutation is downstream from the termination codon of the tat gene, therefore functional tat is produced by this plasmid. The premature termination of Rev is upstream of the leucine stretch known to be essential for the functional domain of Rev.

In the CSF-A/β-gal vector, the production of the assayable marker (β-galactosidase) is negatively regulated by the Rev protein. In the absence of Rev function (as in FS-A/β-gal), a large increase in the production of the assayable marker is seen. Therefore, in the presence of an inhibitor of Rev function, β-galactosidase activity is increased from the construct which produces the Rev protein (CSF-A/β-gal). The construct which lacks the Rev protein (FS-A/β-gal) is not be positively regulated for β-galactosidase production in the presence of this inhibitor and will serve as a control for non-specific increases in β-galactosidase production (not induced by inhibition of Rev function). The specific increase in β-galactosidase production from the Rev producing construct will permit automation and high throughput screening of potential inhibitors of Rev function. Inhibitors of Rev function should serve as inhibitors of viral replication in vivo (in patients infected with HIV). A unique utility of this procedure is in the increase in the assayable marker (β-galactosidase) in the presence of a specific inhibitor of Rev function. The CSF-A/β-gal construct also has the capacity to be analyzed for the production of a Gag protein. The production of this protein is dependent upon Rev, and the expression of this protein will therefore be downregulated in the presence of an inhibitor of Rev function.

Constructs were introduced by electroporation into a cultured T cell line (JM). (Arrigo and Huffinan 1995). Ten million cells were maintained and transfected with 100 μg of either DNA construct in a total volume of 0.5 ml as described (Arrigo and Huffinan 1995). The total DNA in each transfection was adjusted to 100 μg using pCDNA3 (Invitrogen). Half of the cells containing each construct were harvested at day 1 post-transfection. These cells were pelletted by centrifugation at 800 times gravity. Cells were resuspended in 7 ml of PBS (137 mM NaCl, 3 mM KCl, 1.5 mM $KH_2PO_4$, 8 mM $Na_2HPO_4$). 5.7 ml of the cells were pelletted by centrifugation at 800 times gravity. The pellet was resuspended in 100 μl of NP40® lysis buffer (0.65% Nonidet p-40®, 0.15 M NaCl, 10 mM Tris pH 7.8, 1.5 mM $MgCl_2$). The lysed cells were pelletted by centrifugation at 800 times gravity to remove nuclei and particulate debris, and the supernatant (cell extract) transferred to a new tube.

An assay to determine β-galactosidase activity was performed on the supernatant as follows: 70 μl of ONPG (o-Nitrophenyl β-D-Galactopyranoside) (4 mg/ml) in cleavage buffer (60 mM $NA_2HPO_4$—$7H_2O$, 40 mM $NAH_2PO_4$—$H_2O$, 10 mM KCl, 1 mM $MgSO_4$—$7H_2O$) and 200 μl of cleavage buffer with 50 mM β-mercaptoethanol was combined with 30 μl of cell extract or NP40® lysis buffer alone. The reactions were incubated at 37° C. for 30 minutes at which time 0.5 ml of 1 M Sodium Carbonate was added to stop the reaction. The absorbance was read at 420 nanometers. The spectrophotometer was zeroed with the reaction containing NP40® lysis buffer alone. The optical density readings were as follows:

100 μg CSF-A/β-gal (0.300)

100 μg FS-A/β-gal (2.300)

The other half of the cells containing each construct were harvested at day 1 post-transfection. An equivalent number of non-transfected T cells were also harvested. Cell extracts were prepared as above. Assays were performed as above on 30 or 3 μl of extract. The reactions were incubated at 37° C. for 9 (30 μl) or 90 (3 μl) minutes at which time 0.5 ml of 1 M Sodium Carbonate was added to stop the reaction. The absorbance was read at 420 nanometers. The spectrophotometer was zeroed with the reaction containing the cellular extract from non-transfected T cells. The optical density readings were as follows:

30 μl/100 μg CSF-A/β-gal (0.022)

30 μl/100 μg FS--A/β-gal (0.583)

3 μl/100 μg CSF--A/β-gal (0.076)

3 μl/100 μg FS-A/β-gal (0.618)

This assay system demonstrates an 8–80 fold increase in β-galactosidase activity with the construct that contained the Rev mutation (FS-A/β-gal) as compared to the construct expressing wild-type rev (CSF-A/β-gal). Therefore complete inhibition of Rev activity from the wild-type Rev construct, CSF-A/β-gal, will result in a similar increase in β-galactosidase activity.

To further assess the ability to inhibit the Rev protein expressed by the CSF-A/β-gal construct and induce an increase in β-galactosidase activity, an experiment was set up in which 10 million cells were transfected with the combinations of DNAs described below. 90% of the cells were harvested at day 2 post-transfection and resuspended in 200 μl of NP40® lysis buffer. 30 μl of the extracts were incubated for 30 minutes as described above. The absorbance was read at 420 nanometers. The spectrophotometer was zeroed with the reaction containing NP40® lysis buffer alone. The optical density readings were as follows:

50 μg CSF-A/β-gal+50 μg pcTdRev (0.350)

50 μg CSF-A/β-gal+50 μg pCDNA3 (0.000)

50 μg CSF-A/β-gal+50 μg pcCSFRev (0.050)

50 μg FS-A/β-gal+50 μg pcTdRev (0.550)

50 μg FS-A/β-gal+50 μg pCDNA3 (1.200)

50 μg FS-A/β-gal+50 μg pcCSFRev (0.370)

The constructs which were cotransfected with CSF-A/β-gal and FS-A/β-gal express no Rev (pCDNA3), wild-type Rev (pcCSFRev), or a transdominant mutant Rev (pcTdRev). The construct expressing transdominant mutant Rev will therefore be capable of downregulating, in trans, the activity of the wild-type Rev expressed by CSF-A/β-gal. Relative to the transfections with no Rev (pCDNA3) or wild-type Rev (pcCSFRev), the cotransfection of transdominant mutant Rev (pcTdRev) with CSF-A/β-gal results in at least a 7 fold increase in β-galactosidase activity. The cotransfection of transdominant mutant Rev (pcTdRev) with FS-A/β-gal did not demonstrate this increase, relative to controls. The low relative level of β-galactosidase in the transfection of FS-A/β-gal with wild-type Rev demonstrates the ability of wild-type Rev to complement the defective Rev in FS-A/β-gal (i.e. reduce β-galactosidase activity). These results demonstrate that the effect of an inhibitor of Rev function will result in an increased level of β-galactosidase activity from the CSF-A/β-gal construct in a T cell line.

To make this procedure more amenable to high throughput screening, maximization of the detection limits is desirable. Therefore, an experiment was performed in 729 B cells. This cell type allows for high level expression of constructs containing the EBV origin of replication. An experiment was set up in which 20 million cells were transfected with the combinations of DNAs described below. The cells from each transfection were resuspended in 10 ml after transfection. Cells were aliquotted into a 96 well tissue culture microtiter plate; 100, 33, and 10 μl aliquots were dispensed in triplicate. The volumes were all brought to 100 μl with medium. These aliquots represent 1/100, 1/330, 1/1000 of the total transfected cells. Cells were assayed for β-galactosidase activity at day 1 post-transfection. 10 μl of 10% NP40® (in water) was added directly to each sample.

70 μl of ONPG (4 mg/ml) in cleavage buffer (60 mM $NA_2HPO_4$—$7H_2O$, 40 mM $NAH_2PO_4$—$H_2O$, 10 mM KCl, 1 mM $MgSO_4$—$7H_2O$) and 100 μl of cleavage buffer with 100 mM β-mercaptoethanol was added to each sample. The reactions were incubated at 37° C. for 1 hour at which time 100 μl of each reaction was removed and discarded and 100 μl of 1 M Sodium Carbonate was added to stop the reaction. The samples were then read using a Molecular Devices microtiter plate reader at a wavelength of 414 nanometers. The microtiter plate reader was zeroed with the reactions containing cells that were mock transfected. The optical density readings were as follows:

100 μl of cells:

50 μg CSF-A/β-gal+50 μg pcTdRev (1.070, 1.130, 1.120)
50 μg CSF-A/β-gal+50 μg pCDNA3 (.970, 1.060, 1.030)
50 μg CSF-A/β-gal+50 μg pcCSFRev (1.080, 1.000, 1.040)
50 μg FS-A/β-gal+50 μg pcTdRev (1.920, 1.890, 1.900)
50 μg FS-A/β-gal+50 μg pCDNA3 (1.930, 1.890, 1.920)
50 μg FS-A/β-gal+50 μg pcCSFRev (1.910, 1.940, 1.930)

30 μl of cells:

50 μg CSF-A/β-gal+50 μg pcTdRev (0.381, 0.443, 0.331)
50 μg CSF-A/β-gal+50 μg pCDNA3 (0.336, 0.314, 0.325)
50 μg CSF-A/β-gal+50 μg pcCSFRev (0.382, 0.363, 0.356)
50 μg FS-A/β-gal+50 μg pcTdRev (1.950, 1.980, 1.950)
50 μg FS-A/β-gal+50 μg pCDNA3 (1.980, 1.920, 1.980)
50 μg FS-A/β-gal+50 μg pcCSFRev (1.960, 2.020, 1.970)

10 μl of cells:

50 μg CSF-A/β-gal+50 μg pcTdRev (0.144, 0.116, 0.113)
50 μg CSF-A/β-gal+50 μg pCDNA3 (0.113, 0.119, 0.116)
50 μg CSF-A/β-gal+50 μg pcCSFRev (0.147, 0.145, 0.148)
50 μg FS-A/β-gal+50 μg pcTdRev (1.600, 1.490, 1.610)
50 μg FS-A/β-gal+50 μg pCDNA3 (1.610, 1.670, 1.750)
50 μg FS-A/β-gal+50 μg pcCSFRev (1.690, 1.510, 1.630)

These results demonstrate that, in B cells, the mutation in Rev results in a greater than 10 fold increase in β-galactosidase activity. The similar results obtained with the triplicate samples validates the reproducibility of the assay system. The transdominant regulatory effect of pcTdRev was not seen in B cells, which is not unexpected, since the EBV origin of replication, which increases expression in this cell type, is only present within the β-galactosidase producing constructs. (Arrigo et al. (1991)). This will result in much higher expression from the β-galactosidase producing constructs, without a proportional increase in expression from the pcTdRev construct. Therefore, it is likely that not enough transdominant Rev is produced in B cells to inhibit the excess of wild-type Rev.

Easily measurable signal was obtained from 1/1000 of the cells from a single transfection. In fact, the assays performed with 30 or 100 μl of cells resulted in signals that were beyond the range of detection of the assay system. The high sensitivity of this assay will allow the screening of at least 1000 different chemical combinations for an inhibitory effect from a single transfection. Since multiple transfections are easily accomplished, the potential for screening 10,000–100,000 chemical combinations at one time is realistic. The use of a microtiter format, together with a minimal number of manipulations, will allow automation of most of the steps involved. The identification of inhibitors will be straightforward; any compounds which specifically increase β-galactosidase production from CSF-A/β-gal (and not FS-A/β-gal) will be further assessed for inhibition of Rev function. This can be accomplished by assessing the production of a Gag protein by CSF-A/β-gal. An inhibitor of Rev will downregulate Gag and Env production (Campbell et al. 1996), while upregulating β-galactosidase activity.

REFERENCES:

Arrigo, S. J. and Chen, I. S. Y (1991). Rev is necessary for translation but not cytoplasmic accumulation of HIV-1 vif, vpr, and env/vpu-2 RNAs. Genes Devel. 5, 808–819.

Arrigo, S. J., Heaphy, S. and Haines, J. K. (1992). In vivo binding of wild-type and mutant human immunodeficiency virus type 1 Rev proteins: implications for function. J. Virol. 66, 5569–5575.

Arrigo, S. J. and Huffinan, K. (1995). Potent inhibition of human immunodeficiency virus type 1 (HIV-1) replication by inducible expression of HIV-1 PR multimers. J Virol 69, 5988–94.

Arrigo, S. J. Weitsman, S., Rosenblatt, J. D. and Chen, I. S. (1989). Analysis of rev gene function on human immunodeficiency virus type 1 replication in lymphoid cells by using a quantitative polymerase chain reaction method. J. Virol. 63, 4875–81.

Campbell, L. H., Borg, K. T., Arrigo, S. J. (1996). Differential effects of intronic and exonic locations of the human immunodeficiency virus type-1 (HIV-1) Rev-responsive element. Virol. 219, 423–431.

Dayton, E. T., Konings, D. A., Lim, S. Y., Hsu, R. K., Butini, L., Pantaleo, G. and Dayton, A. I. (1993). The RRE of human immunodeficiency virus type 1 contributes to cell-type-specific viral tropism. J Virol 67, 2871–8.

Duan, L., Oakes, J. W., Ferraro, A., Bagasra, O. and Pomerantz, R. J. (1994). Tat and rev differentially affect restricted replication of human immunodeficiency virus type 1 in various cells. Virology 199, 474–8.

Favaro, J. P. and Arrigo, S. J. (1997). Characterization of Rev function using subgenomic and genomic constructs in T and COS cells. In Press 228, Felber, B. K., Drysdale, C. M. and Pavlakis, G. N. (1990). Feedback regulation of human immunodeficiency virus type 1 expression by the Rev protein. J Virol 64, 3734–41.

Gatlin, J., Campbell, L. H., Schmidt, M. G., and Arrigo, S. J. (1995). Direct-Rapid (DR) mutagenesis of large plasmids using PCR. BioTechniques 19, 559–564.

Koyanagi, Y., Miles, S., Mitsuyasu, R. T., Merrill, J. T., Vinters, H. V. and Chen, I. S. Y. (1987). Dual infection of the central nervous system by AIDS viruses with distinct cellular tropisms. Science 236, 819–22.

Malim, M. H. and Cullen, B. R. (1993). Rev and the fate of pre-mRNA in the nucleus: implications for the regulation of RNA processing in eukaryotes. Mol Cell Biol 13, 6180–9.

Neumann, M, Felber, B. K., Kleinschmidt, A., Froese, B., Erfle, V., Pavlakis, G. N. and Brack, W. R. (1995). Restriction of human immunodeficiency virus type 1 production in a human astrocytoma cell line is associated with a cellular block in Rev function. J Virol 69, 2159–67.

What is claimed is:

1. A method of screening for inhibitors of HIV Rev functioning, comprising:
   a) introducing into a cell a nucleic acid construct comprising a reporter gene wherein the reporter gene is positioned in the construct such that expression of the reporter gene is increased when Rev function is decreased and wherein the cell contains Rev;
   b) measuring the expression of the reporter gene;
   c) administering to the cell a potential inhibitor of Rev function;
   d) measuring the expression of the reporter gene; and
   e) comparing the expression of the reporter gene in step (b) to the expression of the reporter gene in step (d); whereby an increase in the expression of the reporter gene in step (b) over the level of expression of the reporter gene in step (d) indicates that the potential inhibitor has inhibited Rev function.

2. A method of screening for inhibitors of HIV Rev functioning comprising:
   a) introducing into a first cell a nucleic acid construct comprising a reporter gene wherein the reporter gene is positioned in the construct such that expression of the reporter gene is increased when Rev function is decreased and wherein the first cell contains Rev;
   b) introducing into a second cell a nucleic acid construct comprising a reporter gene wherein Rev does not affect the expression of the reporter gene;
   c) measuring the expression of the reporter gene in the first cell and the second cell;
   d) administering to the first cell and the second cell the potential inhibitor of Rev function;
   e) measuring the expression of the reporter gene in the first cell and the second cell; and
   f) comparing the expression of the reporter gene before and after administering the potential inhibitor in the first cell and the second cell, thus determining whether the potential inhibitor has increased the expression of the reporter gene in the first cell and the second cell; whereby an increase in the expression of the reporter gene in the second cell correlates to an effect of the potential inhibitor not associated with an inhibition of Rev function, and whereby an increase in the expression of the reporter gene in the first cell that is greater than any increase in expression of the reporter in the second cell indicates that the potential inhibitor is an inhibitor of Rev function.

3. A method of screening for inhibitors of HIV Rev function, comprising:
   a) introducing into a first cell a first nucleic acid construct comprising a reporter gene and introducing into a second cell a second nucleic acid construct comprising a reporter gene, wherein the reporter gene of the first nucleic acid is positioned in the construct such that expression of the reporter gene is increased when Rev function is decreased and wherein Rev does not affect the expression of the reporter gene of the second nucleic acid construct;
   b) administering to the cells a potential inhibitor of Rev function;
   c) monitoring the expression of the reporter genes;
   d) comparing the expression of the reporter gene in the first nucleic acid construct to the expression of the reporter gene in the second nucleic acid construct; and e) correlating a higher level of expression of the reporter gene in the first nucleic acid construct relative to the expression of the reporter gene in the second nucleic acid construct to an inhibition of Rev function, thereby screening for inhibitors of HIV Rev function.

4. A method of screening for inhibitors of HIV Rev functioning, comprising:

a) introducing into a first cell and a second cell a nucleic acid construct comprising a reporter gene wherein the reporter gene is positioned in the construct such that expression of the reporter gene is increased when Rev function is decreased and wherein the first cell and the second cell each contains Rev;

b) administering, to the first cell a potential inhibitor of Rev function;

c) measuring the expression of the reporter gene in the first cell and the second cell; and d) comparing the expression of the reporter gene in the first cell to the expression of the reporter gene in the second cell;

whereby a level of expression of the reporter gene in the first cell that is higher than the level of expression of the reporter gene in the second cell indicates that the potential inhibitor has inhibited Rev function.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO:1:

ACCACCGCGG GTTCACTAAT TGTCCGGATC TGTCTC                     36

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO:2:

ACCACCGCGG ATTCTTAGCA CTTATCTGGG TCG                        33